United States Patent [19]

Brierley et al.

[11] Patent Number: 4,992,179
[45] Date of Patent: Feb. 12, 1991

[54] METAL RECOVERY

[75] Inventors: James A. Brierley; Corale L. Brierley, both of Wheat Ridge, Colo.; Raymond F. Decker, Houghton, Mich.; George M. Goyak, Harmony, Pa.

[73] Assignee: Vistatech Partnership, Ltd., Salt Lake City, Utah

[21] Appl. No.: 439,545

[22] Filed: Nov. 20, 1989

Related U.S. Application Data

[60] Division of Ser. No. 882,763, Jul. 3, 1986, Pat. No. 4,898,827, which is a continuation-in-part of Ser. No. 777,061, Sep. 20, 1985, Pat. No. 4,690,894, which is a continuation-in-part of Ser. No. 661,917, Oct. 17, 1984, abandoned.

[51] Int. Cl.$^5$ ............................................... C02F 1/28
[52] U.S. Cl. .................................... 210/661; 75/722; 210/679; 210/688
[58] Field of Search ............... 210/601, 661, 679, 688, 210/912-914; 75/722

[56] References Cited

PUBLICATIONS

Beveridge et al., "Uptake and Retention of Metals by Cell Walls of *Bacillus subtilis*", *Journal of Bacteriology*, vol. 127, No. 3 (Sep. 1976), pp. 1502-1518.

*Primary Examiner*—Ivars Cintins
*Attorney, Agent, or Firm*—Hopgood, Calimafde, Kalil, Blaustein & Judlowe

[57]     ABSTRACT

A relatively solid, stable biomass reaction product is provided produced from microorganisms having metal uptake properties when contacted by an aqueous solution containing metal cations. The biomass reaction product is produced by treating cells thereof with a caustic solution, whereby the biomass reaction product after drying is characterized in the particulate state of having substantially enhanced uptake of metal cations from aqueous solutions as compared to the metal uptake property of the microorganism before treatment. The biomass reaction product in the particulate state is preferably immobilized in an insoluble binder.

36 Claims, No Drawings

METAL RECOVERY

This application is a division of U.S. Ser. No. 882,763, filed July 3, 1986, now U.S. Pat. No. 4,898,827, which is a continuation-in-part of U.S. patent application Ser. No. 777,061, filed Sept. 20, 1985, now U.S. Pat. No. 4,690,894, which in turn is a continuation-in-part of U.S. application Ser. No. 661,917, filed Oct. 17, 1984, now abandoned.

The present invention is directed to the treatment of aqueous solutions containing cations of heavy metals with a biomass reaction product derived from a microorganism, such as *Bacillus subtilis*, selective to the removal of heavy metals from solution. The invention is also directed to a process of enhancing metal uptake properties of microorganisms and to relatively stable biomass products produced by said process having enhanced metal uptake properties.

BACKGROUND OF THE INVENTION AND THE PRIOR ART

Waste waters from many industrial processes, such as metal finishing, which contain a variety of metal ions some of which are toxic and some of which are valuable, are generated in large quantities. These liquids cannot be released into streams or sewers without causing environmental damage. Furthermore, such release would, in many cases, represent a violation of stringent environmental regulations. Treatment of such waters to remove the metal ions is required. Existing processes for treating such waste waters suffer from many disadvantages, among which are included high cost, production of metal-containing sludges which are difficult to treat for metal recovery and hence are dumped in landfills, complex technology, etc. The use of caustic precipitation, sulfide precipitation, electrolysis, evaporation, reverse osmosis, ion exchange, etc., are all known and suffer from one or more difficulty in terms of energy requirement, limited applicability, low absorption capacity, requirement for precise control, etc.

An attempt to use biomass of living microbes for metal recovery is reported in U.S. Pat. No. 4,293,333. T. J. Beveridge, et al. have reported that cell walls of *B. subtilis* will take up metals from solution (J. Bacteriol. 1976, 127(3), 1502–18). However, living microbes must be cultured, an expensive, capital-intensive process, and are subject to contamination by other microbes and inhibition by high metal concentrations or extremes of pH and other toxic components of waste streams. They are also subject to putrefaction. U.S. Pat. Nos. 4,293,334 and 4,320,093 disclose use of nonliving biomass derived from microbes but these processes display limited metal sorption or uptake capacity.

BRIEF DESCRIPTION OF THE INVENTION

One embodiment of the invention contemplates the recovery of the metal present in cationic form in aqueous streams by using a relatively insoluble solid biomass product in particulate form derived chemically from microorganisms characterized by cell wall structures, a preferred microorganism being the bacterium, *Bacillus subtilis*. The sorption or metal uptake capacity for metal ions is dramatically improved by treating the microorganism with a caustic solution which converts it to a substantially solid biomass reaction product. The term "solid" also includes a reaction product having a porous structure.

The term "caustic" is meant to cover alkaline solutions having a relatively high intrinsic pH, e.g., in excess of 9, preferably in excess of 10 or 11, prior to reaction with the microorganism, the alkaline solution being one which when reacted with a selected microorganism at a pH maintained in excess of 9, preferably maintained in excess of about 10 or 11, produces a relatively solid biomass reaction product having enhanced metal uptake capacity compared to the metal uptake properties of the microorganism prior to the caustic treatment. The term caustic is defined in Webster's Collegiate Dictionary as capable of destroying or eating away by chemical reaction, such as occurs during caustic treatment of microorganisms in accordance with the invention.

The term "sorption" is used in the broad sense to include all forms of metal uptake, whether by adsorption, absorption, ionic bonding, among other forms of metal uptake.

Another embodiment of the invention resides in a process for enhancing the metal uptake properties of microorganisms and the biomass reaction produced by the process. The microorganisms selected are those which have cell wall structures (e.g., *Bacillus subtilis*) which when reacted with a caustic solution at the aforementioned pH's form a substantially solid biomass reaction product having enhanced metal uptake properties. The "causticized" biomass or reaction product having the enhanced uptake capacity is slightly alkaline when dispersed in water. Thus, the invention provides a causticized microorganism in the form of a substantially solid biomass reaction product, the product being preferably in the particulate form.

In producing the solid biomass reaction product, solutions of NaOH and KOH are preferred having concentrations ranging from about 0.25 molar to 1.25 molar. The microorganism, e.g., *Bacillus subtilis*, is treated with the caustic solution at temperatures ranging up to boiling, preferably above ambient temperature, e.g., from about 50° C. to 100° C., to form the biomass reaction product which is then washed to remove excess alkaline solution and then dried. The treated dried biomass may be in the form of hard, grindable bodies, such as plates. The biomass reaction product in the particulate form is slightly alkaline and can be used in a column to contact the metal-containing aqueous stream.

As one example of producing caustic-treated biomass of the *Bacillus subtilis* type, about 300 grams of wet weight biomass is mixed with 1500 ml of 3% NaOH (about 0.75M). The 300 grams of wet weight biomass corresponds to 60 grams dry weight, while the 1500 ml of 3% caustic correspond to about 45 grams of NaOH, the dry weight ratio of biomass to caustic being about 1 to 0.75. The mixture is heated to boiling to form the biomass reaction product which is washed to remove excess alkaline solution and then dried as described hereinabove.

Generally speaking, the dry weight ratio of biomass to caustic may range from 1 part by weight biomass to about ¼ to 3 parts by weight caustic and, more preferably, from about 1 part by weight biomass to about ¼ to 1½ parts by weight caustic, e.g., from about ½ to 1½ parts by weight caustic.

When a metal-containing aqueous stream is contacted with the treated biomass, rapid metal uptake occurs. For example, when the solid biomass reaction product in the particulate state is suspended in the aqueous stream and the biomass particles become loaded with metal, the loaded particles settle readily and can be separated from the aqueous stream by conventional means and the metal values thereof easily recovered.

DETAILED DESCRIPTION OF THE INVENTION

Process waste waters treated in accordance with the invention may contain widely varying amounts of a heavy metal e.g., about 20 milligrams or less to about 2,000 milligrams or more per liter. To be treatable in accordance with the invention, the metal must be in cationic form. Anionic complex ions such as cyanide-metal complexes, may be decomposed by known techniques prior to treatment. Common anions such as sulfates, chlorides, nitrates, phosphates, carbonates, etc., may be present without harm and solutions can successfully be treated over the pH range of about 3 to about 11, preferably about 4 to 8, e.g., about 4 to 6. The heavy metal usually will have an atomic number greater than 20, although aluminum, atomic number 13, can be recovered from aqueous solutions.

The solid biomass product derived from $B.$ $subtilis$ cells is employed in the caustic treated condition, since greater uptake capacity for metal cations thereby results as compared to the untreated $B.$ $subtilis$. As previously stated, the treatment preferably is effected by heating the cell biomass at 50° to 100° C. or boiling, for 1 to 15 minutes with a solution preferably containing about 0.25 molar to about 1.25 molar NaOH concentration. KOH in equivalent amounts may be used. $NH_4OH$ may be employed but is not as effective. Any excess sodium or potassium hydroxide is removed by water washing. The cell biomass may be hydroxylated and/or "cleaned" by removing lipids and other organic matter which masks active sites by the caustic treatment. In any event, metal uptake by the causticized biomass is rapid, the treated biomass exhibiting substantially improved metal uptake capacity relative to the untreated biomass. Treatment with caustic at elevated temperatures, e.g., boiling temperatures, destroys autolytic enzymes (enzymes that the organisms possess that cause putrefaction). Biomass treated with hot or boiling sodium hydroxide solution to kill the cells and inactivate potentially putrefiable matter may be dewatered and dried prior to use. Centrifugation, filtration, etc. may be employed for dewatering. When drying is accomplished in shallow pans, a solid, hard, rock-like plate resembling slate is produced. This hard material can be crushed, ground and sized for use in a metal extraction column. When drying is accomplished in such a manner as to produce the biomass reaction product in powder form, or the product is comminuted, the powder can be agglomerated by employing a binder to immobilize the biomass reaction product and improve the stability and integrity thereof and thereby extend its useful life for use in a metal extraction column. Techniques for agglomerating particulate or powdered material using a binder are well known.

Standard water treatment units may be used for recovering metal ions from solution. For example, processing equipment comprising a mixing unit for contact between cell biomass product and metal-containing liquid may be followed by a settling unit for removing metal-containing particles from suspension with optional final filtration. This characteristic of the particulate biomass facilitates separation from the treated liquid. A continuous or batch-type ultra-filtration polymer membrane unit may be employed for mixing, sorption and filtration. Other modes for contacting metal-containing liquids with solid caustic-treated biomass include, for example, contact of the solution with the treated biomass immobilized in a matrix, such as a gel, for example, agar used as binder, or with a granular biomass contained in a column configuration operated as a packed or fluidized bed. During metal accumulation in caustic-treated biomass, the pH increases even though residual caustic is washed from the treated biomass. It is believed that, at equilibrium, powdered, caustic-treated biomass has greater ultimate metal-loading capacity than coarse granulated, caustic-treated biomass, this being due to the increased surface area of the powdered product. However, it is found that the caustic-treated biomass can be metal saturated more efficiently than powdered biomass reaction product if it is dried, ground, sized, for example to $-35+60$ mesh and then contacted with a continuous flow of metal solution at a given concentration in a packed or fluidized bed contactor. Thus, packed or fluid bed systems containing a microorganism-derived granular biomass reaction product will exhibit enhanced metal-loading capacity when compared to conventional mixing/settling systems using powdered biomass.

It has been observed that copper, silver and gold can be separated from dewatered, loaded biomass reaction product when the moist biomass is contacted with iron. The initial contact can be over a very small area, for example, a scratch in a Teflon-coated steel pan, to initiate separation of metal from the biomass. Once separation of metal is initiated, it continues to form fan-like metal figures radiating from the initial point of contact to produce dendritic-appearing crystals of almost pure metal. Traces of iron are found near the initial contact point. Precipitation of loaded metal appears to proceed on an atom-by-atom basis at relatively low temperatures, e.g., 80° C. This observation indicates that the separation apparently proceeds by galvanic action which may be of value in extracting from solution metals which are below iron in the electromotive series; namely, cadmium, cobalt, nickel, tin, lead, antimony, arsenic, bismuth, copper, mercury, silver, palladium, platinum and gold, among other metals.

Metal can also be recovered pyrolytically from the loaded, dewatered biomass reaction product by fluid-bed combustion or other incineration means using the biomass as fuel.

An example will now be given:

EXAMPLE I

This example demonstrates that metal accumulation in caustic-treated biomass obtained as a biomass reaction product from $B.$ $subtilis$ (ATCC 6051) is greatly enhanced as compared to that obtained with untreated $B.$ $subtilis$ biomass. The $B.$ $subtilis$ employed was produced using a feedstock comprising an aqueous solution containing 12.3 g/l glucose, 5 g/l yeast extract, 1 g/l $KH_2PO_4$, 2 g/l $K_2HPO_4$ and 0.4 g/l $MgSO_4$ at a temperature of 38° C. for 24 hours with mixing at 250 rpm.

Metal accumulation is enhanced when the treated biomass is dried to a hard, solid body, ground and sized, and the biomass product in particulate form contacted countercurrently with a continuous flow of metal solution in a packed or fluidized sorption column. Results obtained in treating dilute silver and copper solutions with caustic-treated biomass as produced after boiling with 0.75M NaOH and which was then dried and ground to −60 mesh are shown in the following Table 1:

TABLE 1

| Test | Treatment | Metal | Initial Metal Concentration in 5 ml of Solution (mg/liter) | mg of Biomass in 5 ml Solution | Sorption (mg metal/g biomass, dry wt) |
|---|---|---|---|---|---|
| 1 | None | $Ag+$ | 94.4 | 40 | 11.4 |
| 2 | Boiled, 0.75M NaOH | $Ag+$ | 101.0 | 1.7 | 54.8 |
| 3 | Boiled, 0.75M NaOH, dried, sized, −60 mesh | $Ag+$ | 110.0 | 2.2 | 86.7 |
| 4 | None | $Cu^{2+}$ | 91.6 | 47 | 9.2 |
| 5 | Boiled, 0.75M NaOH | $Cu^{2+}$ | 97.4 | 1.4 | 35.1 |
| 6 | Boiled, 0.75M NaOH, dried, sized, −60 mesh | $Cu^{2+}$ | 97.1 | 2.2 | 79.2 |

Note: Tests 1 to 6 were conducted batch-wise in a complete mix reactor.

The data shown in Table 1 compare the metal (silver) uptake properties of untreated biomass with caustic-treated biomass, the conditions selected and the amount of biomass employed being such as to achieve equilibrium loading of metal on the biomass in 30 minutes of mixing at 30° C. Referring to Table 1, it will be noted that the untreated biomass (Test 1) exhibited an equilibrium loading of 11.4 mg/gram of biomass (dry weight); whereas, in Test 2, the equilibrium loading increased substantially to 54.8 mg/g of caustic-treated biomass; and in Test 3, the equilibrium loading increased still further to 86.7 mg/g when the biomass was dried and sized to −60 mesh. Similar results are shown for copper in Tests 4 to 6.

A number of other microorganisms, such as *Aspergillus flavus* and *Saccharomyces uvarum*, were given substantially the same caustic treatment as described for *Bacillus subtilis* in Table 1. The NaOH-treated microorganisms tested were examined for metal uptake and were found with respect to certain metal ions to provide improved effectiveness in recovering metal ions from solution, but in some instances, not as effective as the NaOH-treated *Bacillus subtilis*. Examples of such microorganisms are listed in Table 2 below.

Table 2
Microorganisms examined for metal uptake.
Bacteria
  *Escherichia coli*
  *Micrococcus luteus*
  *Pseudomonas aeruginosa*
  *Thiobacillus ferrooxidans*
  TH3, iron oxidizing facultative thermophile
  *Zoogloea ramigera*
Fungi
  *Aspergillus flavus*
  *Cladosporium sp.*
  *Neurospora crassa*
  *Rhizopus stolonifer*
Yeast
  *Saccharomyces uvarum*
Algae
  *Chlorella pyrenoidosa*
  *Ulothrix sp.*

Additional tests with microorganisms have indicated that some microorganisms tended to be more selective to the recovery of certain metal ions than others. For example, a microorganism selected might be superior in metal uptake capacity as to a particular metal ion when compared to *B. subtilis*, while being less effective compared to *B. subtilis* as to another metal ion.

Thus, in carrying out the invention, the microorganism selected is that microorganism which provides enhanced metal uptake capacity as to the particular metal ion of interest, following treatment of the microorganism with caustic. For example, in the treatment of a solution containing metal ions A and B and in which the metal ion of interest is B, the microorganism selected would be one which is particularly selective to the uptake of B. The remaining metal A may then be removed by a biomass reaction product produced from another microorganism more selective to A, although some A may have been taken up by the first biomass reaction product.

Comparative tests were conducted on a series of microorganisms selected from the aforementioned group consisting of bacteria, yeasts, filamentous fungi and algae. In making the comparison, *Bacillus subtilis* was used as a standard. The results indicated that certain of the microorganisms tended to be more selective to the recovery of a particular metal ion than others. As illustrative of this selectively, the following example is given.

EXAMPLE II

Different microorganisms were grown and prepared for comparison of their respective capacity for metal accumulation from solutions containing lead as $Pb(NO_3)_2$ and silver as $AgNO_3$. The microorganisms were tested in the untreated and the caustic-treated state.

Biomass, which was not caustically treated, was harvested from growth medium using centrifugation. The cell paste was washed with water to remove residual medium components and the washed cell paste was oven dried and ground to yield −60 mesh particles. While the dried untreated biomass is a solid, it does not have the hardness of the level obtained with caustic-treated biomass.

Caustic-treated biomass was prepared by mixing cell paste with 3% NaOH, removing residual caustic, washing the paste, oven-drying the paste to yield a hard slate-like material, grinding and sizing the material to −60 mesh.

The oven temperature was in the neighborhood of about 80° C. to 100° C.

One-half gram of each prepared biomass granule (−60 mesh size) was added to 990 ml of an approximate 100 mg metal/liter solution and the solution then shaken for 24 h at 150 rpm and 30° C. (note Table 3). The metal loading of the granules was calculated by determining the initial and final metal concentrations in the test solution. The concentration of metal loaded on the biomass is determined by digesting the biomass in nitric acid or nitric acid plus hydrochloric acid and by measuring the metal concentrations by atomic absorption spectrophotometry of the final solution.

Various conditions were used in carrying out the experiment. The biomass was either not treated with NaOH or treated using 3% NaOH. In determining the effect of pH on metal accumulation, one test was run for lead accumulation using a solution pH adjusted so that the NaOH-treated granules had a test pH near the value of that for the non-treated granules. The results are summarized in Table 3.

granules indicated similar uptake properties regardless of pH (about 9 compared to about 6).

Comparison of the microbes tested with *B. subtilis* showed that most of the microbes exhibited improved metal uptake capacity when treated with caustic. Many of the microbes tested showed higher metal uptake capacity than *B. subtilis*. Other microorganisms, such as *Ps. aeruginosa, S. uvarum* and *A. flavus*, were not as effective, but nevertheless did show improvement with respect to certain metal ions when treated with caustic. However, *B. subtilis* is preferred in that the biomass reaction product produced therefrom is easier to handle when used to recover metal ions from aqueous solutions.

The granules produced from the *B. subtilis*, *E. coli* and *S. uvarum* are relatively solid but not brittle hard.

TABLE 3

Comparative values for silver and lead accumulation by treated and non-treated, granulated microorganisms

| Microorganism | Treatment | Metal | Conc (mg/l) | pH | Metal accumulation (mg/g) | Comparative metal accumulation* |
|---|---|---|---|---|---|---|
| Bacteria | | | | | | |
| Bacillus subtilis | none | Ag | 94 | 5.6 | 45 | 1 |
| | NaOH | Ag | 99 | 9.6 | 65 | 1 |
| | none | Pb | 100 | 5.3 | 74 | 1 |
| | NaOH | Pb | 95 | 9.7 | 174 | 1 |
| | NaOH | Pb | 97 | 6.5 | 170 | 1 |
| Escherichia coli | none | Ag | 95 | 5.5 | 54 | 1.2 |
| | NaOH | Ag | 93 | 10.5 | 106 | 1.6 |
| | none | Pb | 100 | 5.5 | 60 | 0.8 |
| | NaOH | Pb | 91 | 10.7 | 174 | 1.0 |
| | NaOH | Pb | 101 | 6.3 | 180 | 1.1 |
| Pseudomonas aeruginosa | none | Ag | 89 | 5.4 | 36 | 0.8 |
| | NaOH | Ag | 90 | 8.5 | 43 | 0.7 |
| | none | Pb | 87 | 5.3 | 60 | 0.8 |
| | NaOH | Pb | 90 | 9.5 | 142 | 0.8 |
| | NaOH | Pb | 101 | 5.9 | 176 | 1.0 |
| Yeast | | | | | | |
| Saccharomyces uvarum | none | Ag | 100 | 6.1 | 41 | 0.9 |
| | NaOH | Ag | 91 | 6.7 | 18 | 0.3 |
| | none | Pb | 100 | 5.6 | 86 | 1.2 |
| | NaOH | Pb | 97 | 4.5 | 109 | 0.6 |
| Filamentous Fungi | | | | | | |
| Neurospora crassa | none | Ag | 93 | 6.1 | 26 | 0.6 |
| | NaOH | Ag | 96 | 9.1 | 87 | 1.3 |
| | none | Pb | 81 | 4.9 | 75 | 1.0 |
| | NaOH | Pb | 80 | 9.2 | 151 | 0.9 |
| | NaOH | Pb | 101 | 4.7 | 108 | 0.6 |
| Rhizopus arrhizus | none | Ag | 93 | 5.1 | 51 | 1.1 |
| | NaOH | Ag | 84 | 8.3 | 101 | 1.6 |
| | none | Pb | 95 | 4.2 | 118 | 1.6 |
| | NaOH | Pb | 92 | 8.6 | 171 | 1.0 |
| Aspergillus flavus | none | Ag | 94 | 5.5 | 24 | 0.5 |
| | NaOH | Ag | 94 | 8.3 | 94 | 1.4 |
| | none | Pb | 86 | 4.7 | 34 | 0.5 |
| | NaOH | Pb | 96 | 6.6 | 179 | 1.1 |
| Algae | | | | | | |
| Chlorella vulgaris | none | Ag | 95 | 6.9 | 55 | 1.2 |
| | NaOH | Ag | 96 | 8.4 | 115 | 1.8 |
| | none | Pb | 95 | 5.9 | 165 | 2.2 |
| | NaOH | Pb | 95 | 8.7 | 178 | 1.0 |
| | NaOH | Pb | 97 | 5.8 | 188 | 1.1 |
| Chlorella pyrenoidosa | none | Ag | 95 | 6.4 | 38 | 0.8 |
| | NaOH | Ag | 99 | 9.0 | 103 | 1.6 |
| | none | Pb | 95 | 4.8 | 69 | 0.9 |
| | NaOH | Pb | 102 | 9.2 | 175 | 1.0 |
| | NaOH | Pb | 101 | 4.9 | 143 | 0.8 |

*comparative metal accumulation = $\dfrac{\text{mg metal accumulated/g test microbes}}{\text{mg metal accumulated/g B. subtilis}}$ The NaOH treatment enhanced accumulation of silver and lead for every microbe tested except for the yeast, *Saccharomyces uvarum*, which was selective to lead.

The enhanced lead accumulation was not solely an effect of high pH; the pH-adjusted tests using the NaOH The biomass reaction product, depending on the microorganism used, can vary in hardness. However, the product is quite stable and substantially insoluble in aqueous solutions. Biomass reaction products produced from *Ps. aeruginosa, N. crassa, R. arrhizus, A. flavus, C. vulgaris* and *C. pyrenoidosa* were subjectively not as hard as the biomass reaction products of the aforementioned microorganisms. However, they gave very effective results with lead and/or silver.

Not all caustic materials have the same properties of NaOH and KOH in producing granules of biomass reaction product. For example, calcium hydroxide is effective, but not as effective as NaOH. Caustic materials included within the invention are those alkaline materials which convert the microorganism into a biomass reaction product which is substantially solid and stable, capable of forming granules and which granules are substantially insoluble in the aqueous solutions being treated. The term "granules" covers particulate or powdered biomass reaction products of any particle size capable of being easily handled in a system for carrying out the process and includes granules formed from powder using a binder.

Granules of the substantially solid biomass reaction product are advantageous in recovering metal ions from solution in that the granules, because of their low density, can be easily suspended like a fluid bed in a column of solution in which the solution is caused to flow upwardly through a supporting column at a residence time sufficient to effect extraction of the metal ions of interest from the solution.

As the granules or particles of the biomass reaction product become loaded with the metal ions of interest, the granules settle to the bottom of the column from which they are subsequently removed.

A glass column is employed which contains the biomass granules at a specified depth. The dry weight of the granules is recorded. A solution at a specified metal concentration is pumped in the upflow direction through the column. Using this process, tests were conducted on a lead nitrate solution using a biomass reaction product produced from a causticized *B. subtilis*-like biomass. A plurality of one liter solutions, and in some instances two liters, containing lead nitrate were passed separately through the column containing 4 grams of the biomass reaction product until a total of 94 one-liter influent volumes had passed through the column. After passage of each one-liter volume (or two-liter volume), the amount of lead extracted was determined by analyzing each volume of effluent for residual lead. When the percent recovery reaches less than about 90%, the experiment is terminated.

Following termination, the depth of the settled granules and the final weight (dry weight) are determined. The bottom one inch of granules in the column is assayed for metal content; the bottom one inch is assumed to be near saturation loading. The remaining granules in the column are blended and assayed for metal content. The results are given in Table 4. As will be noted, 99% of the metal is removed from the influent solution. This is determined by analyzing the metal content of the effluent solution.

TABLE 4

Removal of cationic lead by granules in upflow column

| | |
|---|---|
| SOLUTION: | Lead Nitrate (Pb(NO$_3$)$_2$) |
| pH OF INFLUENT: | 5 |
| FINAL WEIGHT OF GRANULES AND SORBED Pb: | 5.22 g |
| DEPTH OF GRANULES: | 2 7/8 in. |
| SIZE OF GRANULES: | −35+60 mesh |
| SUPERFICIAL SOLUTION CONTACT TIME: | 1.5 min. |
| ULTIMATE METAL LOADING: | 1150 mg Pb/g granules (dry wt) |
| SPECIAL CONDITIONS: | Shock loadings |

| VOLUME PROCESSED (l) | INFLUENT (mg/l) | EFFLUENT (mg/l) | EFFLUENT pH | PERCENT REMOVAL |
|---|---|---|---|---|
| 1.0 | 8.5 | 0.1 | 9.09 | 99 |
| 2.0 | 8.5 | 0.1 | 8.64 | 99 |
| 3.0 | 8.5 | 0.1 | 8.93 | 99+ |
| 4.0 | 8.5 | 0.1 | 8.74 | 99+ |
| 5.0 | 8.5 | 0.1 | 9.05 | 99+ |
| 6.0 | 8.5 | 0.1 | 8.71 | 99+ |
| 7.0 | 8.5 | 0.3 | 8.33 | 96 |
| 8.0 | 8.5 | 0.1 | 8.63 | 99 |
| 9.0 | 8.5 | 0.1 | 8.57 | 99 |
| 10.0 | 8.5 | 0.1 | 8.66 | 99+ |
| 11.0 | 8.5 | 0.1 | 8.87 | 99+ |
| 12.0 | 8.5 | 0.1 | 8.46 | 99+ |
| 13.0 | 8.3 | 0.1 | 7.01 | 99+ |
| 14.0 | 18.5 | 0.1 | 7.82 | 99+ |
| 15.0 | 18.5 | 0.1 | 7.57 | 99 |
| 16.0 | 18.5 | 0.1 | 7.51 | 99+ |
| 17.0 | 18.5 | 0.1 | 6.14 | 99+ |
| 18.0 | 18.5 | 0.1 | 6.40 | 99+ |
| 19.0 | 18.5 | 0.1 | 6.23 | 99 |
| 20.0 | 508.0 | 0.8 | 7.87 | 99 |
| 21.0 | 17.6 | 0.2 | 8.06 | 99 |
| 22.0 | 17.6 | 0.1 | 7.64 | 99 |
| 23.0 | 17.6 | 0.1 | 7.19 | 99 |
| 24.0 | 17.6 | 0.1 | 7.94 | 99 |
| 25.0 | 494.0 | 118.0 | 5.36 | 76 |
| 26.0 | 8.7 | 5.9 | 5.58 | 32 |
| 27.0 | 8.7 | 0.1 | 6.72 | 99+ |
| 28.0 | 9.2 | 0.1 | 6.98 | 99+ |
| 29.0 | 9.2 | — | — | — |
| 30.0 | 9.2 | — | — | — |
| 31.0 | 9.2 | 0.1 | 6.92 | 99+ |
| 32.0 | 8.9 | 0.1 | 6.64 | 99 |
| 33.0 | 8.9 | 0.1 | 6.31 | 99 |

TABLE 4-continued
Removal of cationic lead by granules in upflow column

| | |
|---|---|
| SOLUTION: | Lead Nitrate (Pb(NO$_3$)$_2$) |
| pH OF INFLUENT: | 5 |
| FINAL WEIGHT OF GRANULES AND SORBED Pb: | 5.22 g |
| DEPTH OF GRANULES: | 2 7/8 in. |
| SIZE OF GRANULES: | −35+60 mesh |
| SUPERFICIAL SOLUTION CONTACT TIME: | 1.5 min. |
| ULTIMATE METAL LOADING: | 1150 mg Pb/g granules (dry wt) |
| SPECIAL CONDITIONS: | Shock loadings |

| VOLUME PROCESSED (l) | INFLUENT (mg/l) | EFFLUENT (mg/l) | EFFLUENT pH | PERCENT REMOVAL |
|---|---|---|---|---|
| 34.0 | 8.9 | 0.1 | 5.82 | 99+ |
| 35.0 | 8.9 | 0.1 | 6.77 | 99+ |
| 36.0 | 8.0 | 0.1 | 6.53 | 99+ |
| 37.0 | 8.0 | 0.1 | 6.16 | 99+ |
| 38.0 | 8.0 | 0.1 | 6.32 | 99+ |
| 39.0 | 7.3 | 0.1 | 6.06 | 99 |
| 40.0 | 7.3 | 0.1 | 6.35 | 99+ |
| 41.0 | 7.3 | 0.1 | 6.56 | 99+ |
| 42.0 | 7.3 | 0.1 | 6.42 | 99+ |
| 43.0 | 7.3 | 0.1 | 6.44 | 99+ |
| 44.0 | 7.3 | 0.1 | 6.14 | 99+ |
| 45.0 | 7.3 | 0.2 | 6.49 | 99 |
| 46.0 | 8.1 | 0.8 | 6.47 | 95 |
| 47.0 | 8.1 | 0.1 | 6.35 | 99+ |
| 48.0 | 8.2 | 0.1 | 6.51 | 99 |
| 49.0 | 8.2 | 0.2 | 6.51 | 99 |
| 50.0 | 8.2 | 0.1 | 6.28 | 99 |
| 51.0 | 8.2 | 0.1 | 5.94 | 99 |
| 52.0 | 8.2 | 0.1 | 6.11 | 99 |
| 53.0 | 20.4 | 0.1 | 6.51 | 99 |
| 55.0 | 20.4 | 0.2 | 6.25 | 99 |
| 57.0 | 20.1 | 0.1 | 6.32 | 99+ |
| 59.0 | 20.1 | 0.1 | 6.90 | 99 |
| 61.0 | 20.1 | 0.1 | 6.66 | 99+ |
| 63.0 | 16.8 | 0.1 | 6.50 | 99+ |
| 65.0 | 16.8 | 0.1 | 6.17 | 99+ |
| 67.0 | 16.8 | 0.1 | 6.24 | 99 |
| 69.0 | 19.0 | 0.1 | 5.63 | 99+ |
| 71.0 | 19.0 | 0.1 | 5.67 | 99 |
| 73.0 | 18.8 | 0.1 | 6.42 | 99 |
| 75.0 | 18.8 | 0.1 | 6.53 | 99+ |
| 77.0 | 18.8 | 0.1 | 6.25 | 99+ |
| 79.0 | 18.8 | 0.2 | 6.09 | 99 |
| 81.0 | 19.8 | 0.4 | — | 98 |
| 83.0 | 19.8 | 0.3 | 5.96 | 98 |
| 85.0 | 19.8 | 0.1 | 5.98 | 99 |
| 87.0 | 19.2 | 0.2 | 6.03 | 99 |
| 89.0 | 19.2 | 0.8 | — | 96 |
| 91.0 | 18.9 | 0.8 | 5.90 | 96 |
| 93.0 | 18.9 | 4.6 | 5.53 | 76 |
| 94.0 | 18.9 | 1.5 | 5.44 | 92 |

The solutions tested were dilute, except for two solutions (volumes 20 and 25) which contained shock loadings of 508 and 494 mg/l of lead, respectively. Each pass-through of solution from volumes 1 to 87 showed substantial removal of lead of about 99% for each volume. This test illustrates the very high metal uptake capacity of the biomass reaction product, despite the shock loading of volumes 20 and 25.

The shock loading of volume 25 resulted in a removal of 76% which returned to 99% when a more dilute solution (8.7 or 9.2 mg/l) was used. The drop to 32% removal with volume 26 is due to retained amounts of the shock solution of volume 25. Following washing out of the shock solution with subsequent dilute solutions, the percent recovery returned to 99% as shown by volumes 27, 28, etc.

It should be noted that the metal loading of 1150 mg Pb/g of granules is for the bottom one inch of the column, while the granules near the top assayed 802 mg Pb/g. The amount of lead accumulated was determined by solution analysis to be about 2.22 g. Analysis of the loaded granules showed a lead recovery of about 2.46 g, which calculates to an acceptable deviation of about 10%. Substantially all of the lead was removed from the solution by the granules.

Additional tests were conducted on copper sulfate solution. These tests are reported in Tables 5 and 6. The solutions treated in Table 5 had a fairly high influent loading of copper of about 100 mg/l; whereas, in Table 6, the influent loading of copper was much lower and ranged from about 8.5 to 9.5 mg/l of copper.

Both tests showed a fairly high metal uptake capacity of the biomass reaction product.

TABLE 5

Removal of cationic copper by granules in upflow column
(influent = 100 mg/Cu/l)

| | |
|---|---|
| SOLUTION: | Copper Sulfate (CuSO$_4$) |
| pH OF INFLUENT: | 5 |
| FINAL WEIGHT OF GRANULES AND SORBED Cu: | 5.75 g |
| DEPTH OF GRANULES: | 3.75 in. |
| SIZE OF GRANULES: | −35 +60 mesh |
| SUPERFICIAL SOLUTION CONTACT TIME: | 2.3 min. |
| ULTIMATE METAL LOADING: | 150.7 mg Cu/g granules (dry wt) |
| SPECIAL CONDITIONS: | none |

| VOLUME PROCESSED (l) | INFLUENT (mg/l) | EFFLUENT (mg/l) | EFFLUENT pH | PERCENT REMOVAL |
|---|---|---|---|---|
| 1 | 100 | 0.1 | 7.3 | 99+ |
| 2 | 100 | 0.3 | 6.9 | 99 |
| 3 | 100 | 2.5 | 6.2 | 97 |
| 5 | 100 | 6.1 | 6.2 | 94 |
| 7 | 100 | 24.8 | 5.6 | 75 |
| 9 | 100 | 49.7 | 5.0 | 50 |

The copper loading of the granules of 150.7 mg Cu/g was determined for the bottom one inch of the column, the total amount accumulated by the granules being about 796 mg. The amount removed from the solution was determined to be about 741 mg, which calculates to an acceptable deviation of about 7%.

TABLE 6

Removal of cationic copper by granules in upflow column
(influent = 10 mg/Cu/l)

| | |
|---|---|
| SOLUTION: | Copper Sulfate (CuSO$_4$) |
| pH OF INFLUENT: | 5.41 |
| FINAL WEIGHT OF GRANULES AND SORBED Cu: | 6.5 g |
| DEPTH OF GRANULES: | 4.16 in. |
| SIZE OF GRANULES: | −35 +60 mesh |
| SUPERFICIAL SOLUTION CONTACT TIME: | 2.3 min. |
| ULTIMATE METAL LOADING: | 140 mg Cu/g granules (dry wt) |
| SPECIAL CONDITIONS: | none |

| VOLUME PROCESSED (l) | INFLUENT (mg/l) | EFFLUENT (mg/l) | EFFLUENT pH | PERCENT REMOVAL |
|---|---|---|---|---|
| 1 | 8.5 | 0.1 | 9.66 | 99 |
| 2 | 8.5 | 0.2 | 7.94 | 98 |
| 3 | 8.5 | 0.3 | 6.94 | 96 |
| 5 | 9.1 | 0.1 | 6.93 | 99 |
| 7 | 9.1 | 0.1 | 6.83 | 99+ |
| 9 | 9.2 | 0.1 | 7.31 | 99+ |
| 11 | 9.2 | 0.1 | 6.85 | 99+ |
| 13 | 9.2 | 0.1 | 6.42 | 99 |
| 15 | 9.3 | 0.1 | 6.85 | 99 |
| 17 | 9.3 | 0.2 | 7.05 | 98 |
| 19 | 9.6 | 0.1 | 6.54 | 99+ |
| 21 | 9.6 | 0.1 | 6.53 | 99+ |
| 23 | 9.5 | 0.4 | — | 96 |
| 25 | 9.5 | 0.4 | 6.56 | 96 |
| 27 | 9.5 | 0.1 | 7.06 | 99+ |
| 29 | 8.5 | 0.1 | 7.45 | 99+ |
| 31 | 8.5 | 0.1 | 7.68 | 99+ |
| 33 | 8.5 | 0.1 | 7.05 | 99+ |
| 35 | 8.5 | 0.1 | 6.75 | 99+ |
| 37 | 9.0 | 0.1 | 6.77 | 99 |
| 39 | 9.0 | 0.1 | 6.87 | 99 |
| 41 | 9.0 | 0.1 | 6.89 | 99+ |
| 43 | 9.0 | 0.1 | 6.95 | 99+ |
| 45 | 9.0 | 0.1 | 6.74 | 99 |
| 47 | 9.4 | 0.1 | 6.81 | 99 |
| 49 | 9.4 | 0.2 | 6.48 | 98 |
| 51 | 9.4 | 0.1 | 6.64 | 99 |
| 53 | 9.4 | 0.2 | 6.31 | 98 |
| 55 | 9.0 | 0.8 | 5.85 | 91 |
| 57 | 9.0 | 1.1 | 5.98 | 88 |
| 58 | 9.0 | 1.2 | 5.96 | 87 |

The copper loading of the granules was determined for the bottom one inch of the upflow column to be about 140 mg Cu/g, the total amount accumulated determined by analysis being about 507 mg. The amount of copper removed based on solution analysis was about 500 mg, which calculated to a deviation of about 1.4%.

Additional tests were conducted with granules of caustic-treated *B. subtilis* produced in accordance with the invention in which other metal ions were recovered from solution, such as cadmium, zinc and gold.

With regard to cadmium and zinc, two separate metal-loading tests were conducted using a cylindrical column having confined therein a granule bed of the caustic-treated biomass measuring about 1.7 centimeters in diameter and 10 centimeters high, the biomass having a granule size of about −35 mesh +60 mesh. The cadmium solution contained 100 mg Cd per liter as $CdCl_2$, and the zinc solution contained 100 mg Zn per liter as $ZnSO_4$. Each of the solutions was passed upward through its respective column at a rate of 10 ml per minute. The test for each was terminated when less than 90% of the metal was removed from the solution.

The granules at the bottom 2.54 cm of the column were analyzed for metal content and the data showed that each of the metals was accumulated. In the case of cadmium, the loading of the bottom 2.54 cm of the bed was 111 mg/g. In the case of zinc, the loading for the bottom 2.54 cm of the bed was 80 mg/g.

The test conducted on a gold solution likewise showed that gold was accumulated by the caustic-treated B. subtilis. In this test, a column containing 1 gram of caustic-treated B. subtilis was used, the size of the granules being about −35 mesh +60 mesh. The gold solution employed contained 896 mg Au per liter, the amount of solution treated being 450 ml. The solution was passed upward through the bed at a rate of 7.5 ml per minute. The 1 gram bed assayed 193 mg Au/g.

As will be apparent from the tests summarized in Tables 4 to 6, and the additional tests on Cd, Zn and Au, a biomass reaction product may exhibit different metal uptake properties for different metal ions. Likewise, as will be apparent from Table 3, different biomass reaction products exhibit different selectivity for different metal ions.

Despite such differences, the biomass reaction products described herein have great utility. For example, where it is desired to clean up wastewater containing toxic metal ions, at least two of which are selective to different biomass products, a mixture of two or more biomass products may be employed to remove the toxic elements.

Since many streams contain multiple metal cations, sorption competition may occur between the various cations with respect to the caustic-treated biomass. Batch tests were run for mixed-metal metal sorption by granules produced by caustic-treated B. subtilis. Two metal pairs were used, copper plus nickel and chromium plus nickel. For each pair, three sorption experiments were conducted, varying the metals concentrations in ratios of 1:3, 2:2, and 3:1 with a total metal content of about 200 mg/l (see Table 7 below). Both copper and nickel were sorbed with nearly equal efficiency (62–72%), and there was good agreement for sorption determined by solution metal concentrations or granule metal concentration. The copper at the highest concentration (146 mg/l) had the greater sorption and the greater percent of removal by the biomass. However, the percent nickel removal was better at lower concentrations (50–100 mg/l) regardless of mix with copper or chromium. When chromium and nickel were mixed, there was less total metals sorption. Perhaps the trivalent chromium complexed additional anionic surface sites and prevented sorption of more chromium or nickel.

TABLE 7

| Initial Metal Conc. mg/l | Final Metal Conc. mg/l | Removal % | Sorption Based on Solution Concs. mg/g | Sorption Based on Solid Conc. mg/g | Initial Metal Conc. mg/l | Final Metal Conc. mg/l | Removal % | Sorption Based on Solution Concs. mg/g | Sorption Based on Solid Conc. mg/g | Total Metals From Solids mg/g |
|---|---|---|---|---|---|---|---|---|---|---|
| COPPER ($CuSO_4$) | | | | | NICKEL ($NiSO_4$) | | | | | |
| 48.3 | 18.3 | 62 | 3.0 | 5.9 | 144 | 55.4 | 62 | 8.9 | 10.6 | 16.5 |
| 99.8 | 31.4 | 68 | 6.8 | 10.5 | 100 | 33.2 | 67 | 6.7 | 7.8 | 18.3 |
| 146 | 41.1 | 72 | 10.5 | 14.2 | 49.6 | 15.8 | 68 | 3.4 | 4.1 | 18.3 |
| CHROMIUM ($CrCl_3$) | | | | | NICKEL ($NiSO_4$) | | | | | |
| 47.4 | 36.0 | 24 | 1.1 | 1.0 | 146 | 77.8 | 47 | 6.8 | 7.3 | 8.3 |
| 99.8 | 50.4 | 49 | 4.9 | 3.5 | 106 | 52.0 | 51 | 5.4 | 4.9 | 8.4 |
| 150 | 46.6 | 69 | 10.3 | 8.1 | 56.4 | 20.2 | 64 | 3.6 | 3.3 | 11.4 |

As stated hereinbefore, other modes for contacting metal-containing solutions with solid caustic-treated biomass may be employed. For example, the caustic-treated biomass may be immobilized in a matrix using a binder in order to increase the stability of the biomass and extend its useful life. One method is to immobilize the caustic-treated biomass in agar. In one example, caustically treated, but not dried, Bacillus subtilis (American Type Culture Collection [ATCC 6051]) was embedded in a gel of agar (acid ester of a linear galactan) and the gel-cells in the form of small fragments were used to obtain sorption isotherms for copper and silver. Since agar alone will sorb such metals, agar alone was compared with agar plus B. subtilis.

In the case of a copper solution containing 18.6 mg/liter of copper, agar alone removed about 30% of copper; whereas, agar plus B. subtilis removed about 66% from solution. In a starting solution containing 98.2 mg/l of copper, the agar removed only about 14.6%; whereas, the agar plus B. subtilis removed 70%. It was noted that as the starting solution increases in copper concentration, the percent removal of copper with agar plus biomass decreases as the loading of the biomass approaches saturation. Tests with silver gave similar results. For example, at a starting silver concentration in solution of 18.3 mg/l, the agar exhibited a percent removal of silver of about 60% in thirty minutes as compared to 71% for agar plus B. subtilis. However, at a silver concentration of 95.7 mg/l, the percent removal of silver with agar alone dropped to 23%; whereas, the immobilized caustic-treated biomass (agar plus B. subtilis) exhibited an increase in silver recovery to 83%.

A preferred method of immobilizing caustic-treated biomass and of extending its useful life is to agglomerate the biomass using an insoluble binder and provide hardened granules thereof. Binders which may be employed include polymerizable resins, for example, components of formaldehyde, monofunctional aldehydes, glyoxal, glutaraldehyde, or other polyfunctional aldehydes. Dextrose may also be employed.

The amount of binder used should be at least 0.5% by weight of the agglomerate taken on the dry basis, but not be so high as to substantially adversely affect the metal uptake properties of the caustic-treated biomass. The amount of binder mixed with the caustic-treated biomass on the dry basis may range by weight from about 0.5% to 10% of the agglomerate.

The binder may be added to the caustic-treated biomass paste before drying and the dried product then comminuted and sieved to a desired particle size, e.g., −35+60 mesh (Tyler Standard Screen).

A test conducted on granules of caustic-treated *B. subtilis*-like biomass containing glyoxal as a hardener, with and without other additives, indicated there was no significant effect from glyoxal on copper uptake. The caustic-treated biomass without a binder exhibited a copper uptake from a copper sulfate solution at substantially equilibrium loading of about 109 mg Cu/g. When 0.5% by weight of glyoxal was used as a binder, the copper uptake was about 111 mg Cu/g.

When 1% glyoxal was used as a binder, the copper uptake was about 121 mg Cu/g. The combination of 1% glyoxal and 0.1% NaCl by weight of the granule resulted in copper uptake of about 110 mg Cu/g. When 1% glyoxal and 0.1% dextrose was used by weight of the granules, the copper uptake was 115 mg Cu/g. The tests indicated that at least 0.5% glyoxal by weight was sufficient to provide satisfactory hardening and stability. The granules with 1% glyoxal/0.1% NaCl and 1% glyoxal/0.1% dextrose exhibited good stability.

Increasing the glyoxal content from 0.5% to 5% by weight resulted in the formation of harder granules. In adding the glyoxal to dried caustic-treated *B. subtilis*-like biomass, 125 grams were suspended in 500 ml of glyoxal solution, the amount of glyoxal being sufficient to provide the desired weight percent with the biomass on the dry basis.

The solution with the biomass was decanted and the treated granules were dried at 80° to 100° C. The residue is either reground, or sieved, or simply crushed to obtain the desired particle size and provide granules of biomass immobilized in the glyoxal binder. While the useful life of the granules with the binder is increased, however, with time some granule attrition occurs.

With regard to the caustic reagent used to carry out the invention, it has been found that a strong detergent material sold under the trademark "ALCONOX" appears to act similarly to sodium hydroxide in treating *B. subtilis*. This detergent is a long chain alkyl sulfonate which is a wetting agent. It is biodegradable. It contains about 7.3% phosphorus by weight as trisodium phosphate. The pH of the detergent is 9 to 9.5.

Attempts have been made to explain the reason for the selective behavior of caustic-treated microorganisms. While we do not wish to be held to any particular theory, it has been stated that the cell walls of *Bacillus subtilis* (a Gram-positive bacterium) are considered to be polymeric in nature including strands of mucopeptides (peptidoglycans), teichoic acids or teichuronic acids distributed and attached along their length. The long polymers comprising the mucopeptides are composed of three kinds of building blocks; namely, N-acetylglucosamine (AGA), N-acetylmuramic acid (AMA), and a peptide consisting of four or five amino acids; i.e., L-alanine, D-alanine, D-glutamic acid and either lysine or diaminopimelic acid. A substantial proportion, e.g., about 35% of the mucopeptide strands are cross-linked together through transpeptide (D-alanyl-(L)-meso-diaminopimelyl) bonds. The polymeric structure possesses chemically reactive groups including oxygen, nitrogen, sulfur and phosphorus which carry lone electron pairs that bind metals. Such atoms are effective as electron donors for metal ions. The effects of sodium hydroxide upon such materials are not readily evident although, inter alia, it is believed sodium hydroxide removes lipids and other organic impurities that mask reactive sites. Caustic-treated cell wall material from other Gram-positive bacilli having mucopeptide strands cross-linked with peptide bonds and reacting similarly to caustic treatment may also be employed in accordance with the invention.

The Gram-negative bacterium, *E. coli*, is also particularly useful as a starting material, in carrying out the invention.

Conversion of the caustic-treated biomass derived from *B. subtilis* cells into particles by drying to a hard or solid body and grinding facilitates handling and promotes treatment of metal-containing aqueous streams to recover the metal content thereof by continuous counter-current decantation, by pulsed bed, fluid bed and other technologies in which a column of liquid undergoing treatment can be employed. A bed of ground particles contacted with an upwardly-flowing metal-containing stream can become classified with coarser particles in the lower portion of the bed and finer, more active particles in the upper portion of the bed. In this way, the coarser particles contact fresh feed while the finer particles contact a partially metal depleted stream. This action promotes high loading of the particles and high recovery of metal from the incoming stream.

In summary, the invention comprises various embodiments.

One embodiment is directed to a process for enhancing the metal uptake properties of *Bacillus subtilis* from aqueous solutions containing metal cations in which cells of the bacterium, *Bacillus subtilis*, are treated with a caustic solution to form a causticized material consisting essentially of a biomass reaction product. In another embodiment, the biomass reaction product is recovered and dried to form a relatively solid, stable product. The biomass reaction product in the particulate state exhibits substantially enhanced metal uptake capacity as compared to the metal uptake capacity of the *Bacillus subtilis* in the untreated state. A preferred caustic solution is one selected from the group consisting of NaOH and KOH.

As stated herein, the caustic treatment may be carried out at temperatures ranging up to boiling and preferably over a temperature range of about 50° C. to about 100° C.

The process is applicable to a relatively broad range of microorganisms provided they are characterized by cell wall structures. Thus, the process is applicable to cells of bacilli, such as Gram-positive bacteria (e.g., *B. subtilis*) and Gram-negative bacteria (e.g., *E. coli*). Examples of microorganisms are bacteria, yeast, fungi and algae, so long as the microorganism is characterized by a cell wall structure and is selective to uptake of metal ions, and which when treated with a caustic solution produces a relatively solid, stable biomass reaction product having substantially enhanced metal uptake capacity for metal ions compared to the uptake capacity before treatment.

The biomass reaction product of the invention consists essentially of a causticized non-living microorganism.

A particular advantage of the invention is that a microorganism-derived biomass reaction product, in the form of a solid, stable particulate material, can be used as a fluid bed in an aqueous solution containing metal cations with the solution flowing countercurrently through the bed. As the particles of the bed become loaded, they segregate to a lower part of the bed from which they can be removed for the subsequent recovery of metal therefrom.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

What is claimed is:

1. A process for treating an aqueous solution containing at least one heavy metal cation to remove said cation by sorption and recover said metal which comprises:

providing a biomass of the bacterium *Bacillus subtilis* characterized by cell walls and which is selective to the sorption of said at least one heavy metal cation, which bacterium has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed to remove excess alkaline solution therefrom and then immobilized in an insoluble binder, contacting said solution with an amount of said immobilized biomass reaction product in granular form sufficient to sorb said cation into said biomass product, and thereafter separating the resulting metal-containing biomass from said solution.

2. The process in accordance with claim 1, wherein said metal-containing solution is a waste water solution containing up to about two grams per liter of said metal cation.

3. The process of claim 1, wherein the heavy metal cation is sorbed by the granular biomass while said biomass is suspended in said aqueous solution.

4. The process in accordance with claim 3, wherein said aqueous solution is a wastewater stream.

5. A process for treating an aqueous solution containing at least one heavy metal cation to remove said cation by sorption and recover said metal which comprises:

providing a biomass of the bacterium *Bacillus subtilis* characterized by cell walls and which is selective to the sorption of said at least one heavy metal cation, which bacterium has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried to a hard grindable body and ground to granular form and immobilized in an insoluble binder, contacting said solution with an amount of said granular biomass reaction product sufficient to sorb said cation into said biomass product, and thereafter separating the resulting metal-containing biomass from said solution.

6. The process of claim 5, wherein the amount of insoluble binder by weight ranges from about 0.5% to 10%.

7. The process of claim 5, wherein the heavy metal cation is sorbed by the granular biomass while said biomass is suspended in said aqueous solution.

8. The process in accordance with claim 5, wherein said granular biomass product is supported as a packed column and the solution to be treated passed through said column in an upflow direction.

9. The process in accordance with claim 5, wherein said granular biomass product is supported as a packed column and the solution to be treated passed through said column in a downflow direction.

10. The process in accordance with claim 5, wherein said granular biomass product is disposed as a fluid bed, in a column of said solution to be treated, with the solution passing through said column in the upflow direction.

11. The process in accordance with claim 5, wherein said granular biomass reaction product is supported in a column, and wherein said biomass column is disposed as a pulsed bed, with said aqueous solution moving upwardly in said column, with fresh treated biomass product introduced at substantially the top of said column while metal-laden biomass is removed from substantially the bottom of said column.

12. The process in accordance with claim 5, wherein said granular biomass is provided as a packed column, and wherein the aqueous solution to be treated is passed through the column.

13. A process for treating an aqueous solution containing at least one heavy metal cation to remove said cation by sorption and recover said metal which comprises:

providing a biomass of the bacterium *Bacillus subtilis* characterized by cell walls and which is selective to the sorption of said at least one heavy metal cation, which bacterium has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass product is washed, dried to a hard grindable body and ground to granular form and immobilized in an insoluble binder, to provide a variety of particle sizes which are disposed in an upflow column, and passing said solution through said upflow column of said granular biomass reaction product at a rate to cause stratification of said biomass with larger biomass particles in the lower portion of said column and finer biomass particles in the upper portions of said column, whereby the smaller and more active biomass particles contact said solution to remove metal cations by sorption after the bulk of said cations have been removed therefrom by said larger particles.

14. The process of claim 13, wherein the amount of insoluble binder by weight ranges from about 0.5% to 10%.

15. A process for treating an aqueous solution containing at least one heavy metal cation to remove said cation by sorption and recover said metal which comprises:

provided a biomass of a Gram-positive bacterium characterized by polymeric cell wall material derived from a Gram-positive bacterium having mucopeptide strands cross-linked with transpeptide bonds and which is selective to the sorption of said at least one heavy metal cation and which bacterium has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried, and immobilized in an insoluble binder, contacting said solution with an amount of said biomass reaction product in granular form sufficient to sorb said cation into said biomass product, and thereafter separating the resulting metal-containing biomass from said solution.

16. The process in accordance with claim 15, wherein said metal-containing solution is a waste water solution containing up to about two grams per liter of said metal.

17. The process in accordance with claim 15, wherein the heavy metal cation is sorbed by the granular biomass while said biomass is suspended in said aqueous solution.

18. The process according to claim 15, wherein said granular biomass is provided as a packed column, and wherein the aqueous solution to be treated is passed through said column.

19. A process for treating an aqueous solution containing at least one heavy metal cation to remove said cation by sorption and recover said metal which comprises:

providing a biomass of bacterium characterized by cell walls and which is selective to the sorption of said at least one heavy metal cation and which bacterium has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried, and immobilized in an insoluble binder, contacting said solution with an amount of said biomass reaction product in granular form sufficient to sorb said cation into said biomass product, and thereafter separating the resulting metal-containing biomass from said solution.

20. The process of claim 19, wherein the heavy metal cation is sorbed by the granular biomass while said biomass is suspended in said aqueous solution.

21. The process in accordance with claim 19, wherein said granular biomass product is supported as a packed column and the solution to be treated passed through said column in the upflow direction.

22. The process of claim 19, wherein the amount of insoluble binder by weight ranges from about 0.5% to 10%.

23. The process in accordance with claim 19, wherein said granular biomass product is supported as a packed column and the solution to be treated passed through said column in the downflow direction.

24. The process in accordance with claim 19, wherein said granular biomass product is disposed as a fluid bed, in a column of said solution to be treated, with the solution passing through said column in the upflow direction.

25. The process of claim 19, wherein said granular biomass is provided as a packed column, and wherein the aqueous solution to be treated is passed through said column.

26. A process for treating an aqueous solution containing at least one heavy metal cation to remove said cation by sorption and recover said metal which comprises:

providing a biomass of a bacterium characterized by cell walls and which is selective to the sorption of said at least one heavy metal cation characterized by cell walls, which bacterium has been treated with an amount of a caustic solution maintained at elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried, and immobilized in an insoluble binder to provide a hard grindable body and ground to granular form to provide a variety of particle sizes which are disposed in an upflow column, and passing said solution through said upflow column of said granular biomass reaction product at a rate to cause stratification of said biomass with larger biomass particles in the lower portion of said column and finer biomass particles in the upper portions of said column, whereby the smaller and more active biomass particles contact said solution to remove metal cations by sorption after the bulk of said cations have been removed therefrom by said larger particles.

27. A process for treating an aqueous solution containing at least one heavy metal cation to remove said cation by sorption and recover said metal which comprises:

providing a biomass characterized by cell walls of a microorganism selected from the group consisting Saccharomyces, Neurospora, Rhizopus and Aspergillus, and which is selective to the sorption of said at least one heavy metal cation, which microorganism has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried and immobilized in an insoluble binder, contacting said solution with an amount of said biomass reaction product in granular form sufficient to sorb said cation into said biomass product, and thereafter separating the resulting metal-containing biomass from said solution.

28. The process in accordance with claim 27, wherein said metal-containing solution is a waste water solution containing up to about two grams per liter of said metal.

29. The process in accordance with claim 27, wherein said aqueous solution is a waste-water stream, and wherein said granular biomass reaction product is suspended in said stream.

30. The process of claim 27, wherein the amount of insoluble binder by weight ranges from about 0.5% to 10%.

31. A process for treating an aqueous solution containing at least one heavy metal cation to remove said cation by sorption and recover said metal which comprises:

providing a biomass characterized by cell walls of a microorganism selected from the group consisting Saccharomyces, Neuropora, Rhizopus and Aspergillus, and which is selective to the sorption of said at least one heavy metal cation, which microorganism has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried and immobilized in an insoluble binder to provide a hard grindable body and ground to granular form to provide a variety of particle sizes which are disposed in an upflow column, and passing said solution through said upflow column of said granular biomass reaction product at a rate to cause stratification of said biomass with larger biomass particles in the lower portion of said column and finer biomass particles in the upper portions of said column, whereby the smaller and more active biomass particles contact said solution to remove metal cations by sorption after the bulk of said cations have been removed therefrom by said larger particles.

32. The process according to claim 31, wherein the amount of binder by weight ranges from about 0.5% to 10%.

33. A process for treating an aqueous solution containing a least one heavy metal cation to remove said cation by sorption and recover said metal which comprises:

providing a biomass characterized by cell walls of a microorganism which is selective to the sorption of said at least one heavy metal cation, which microorganism has been treated with an amount of a caustic solution maintained at an elevated temperature above ambient and ranging up to boiling at a pH in excess of 9 sufficient to form a causticized biomass reaction product consisting essentially of material derived from the cell walls thereof having enhanced metal uptake properties following which said biomass reaction product is washed, dried and immobilized in an insoluble binder, contacting said solution with an amount of said biomass reaction product in granular form sufficient to sorb said cation into said biomass product, and thereafter separating the resulting metal-containing biomass from said solution.

34. The process in accordance with claim 33, wherein said metal-containing solution is a waste water solution containing up to about two grams per liter of said metal.

35. The process in accordance with claim 33, wherein said aqueous solution is a waste water stream, and wherein said granular biomass reaction product is suspended in said stream.

36. The process of claim 33, wherein said granular biomass is provided as a packed column, and wherein the aqueous solution to be treated is passed through said column.

* * * * *